United States Patent [19]

Bloch

[11] 3,953,522

[45] Apr. 27, 1976

[54] PROCESS FOR THE PREPARATION OF N-ALKYL-SUBSTITUTED HYDROXYPOLYALKOXYMETHYLCYCLOHEXANES

[75] Inventor: Herman S. Bloch, Skokie, Ill.

[73] Assignee: Universal Oil Products Company, Des Plaines, Ill.

[22] Filed: Nov. 4, 1974

[21] Appl. No.: 520,694

Related U.S. Application Data

[63] Continuation-in-part of Ser. No. 277,835, Aug. 3, 1972, Pat. No. 3,859,324.

[52] U.S. Cl............................................ 260/611 B
[51] Int. Cl.² ..................................... C07C 41/02
[58] Field of Search.......... 260/611 B, 611 F, 617 R

[56] References Cited
UNITED STATES PATENTS 3,859,324   1/1975   Bloch................................ 260/457

*Primary Examiner*—Bernard Helfin
*Attorney, Agent, or Firm*—James R. Hoatson, Jr.; Raymond H. Nelson; William H. Page, II

[57] ABSTRACT

Non-ionic biodegradable detergents as exemplified by n-alkyl-substituted hydroxypolyalkoxymethylcyclohexanes may be prepared by condensing butadiene with allyl alcohol, selectively hydrogenating the resulting compound to form hydroxymethylcyclohexane, ring alkylating said substituted cyclohexane with an olefin in the presence of a free-radical generating compound to form an alkyl-substituted hydroxymethylcyclohexane and thereafter alkoxylating this compound to form the desired product.

7 Claims, No Drawings

PROCESS FOR THE PREPARATION OF N-ALKYL-SUBSTITUTED HYDROXYPOLYALKOXYMETHYLCYCLOHEXANES

CROSS-REFERENCE TO RELATED APPLICATIONS

This application is a continuation-in-part of my co-pending application Ser. No. 277,835 filed Aug. 3, 1972, now U.S. Pat. No. 3,859,324, Jan. 7, 1975, all the teachings of which are incorporated herein by reference.

This invention relates to a process for preparing non-ionic biodegradable detergents. More specifically, the invention is concerned with a novel method comprising a series of steps hereinafter set forth in greater detail whereby n-alkyl-substituted hydroxypolyalkoxymethylcyclohexanes are formed.

One of the major problems which is prevalent in population centers throughout the world is the disposal of sewage containing detergents dissolved therein. Such disposal problems are especially trying in the case of branch-chained alkylaryl detergents. These detergents produce stable forms in hard or soft waters in such large quantities that the foam clogs sewage treatment facilities, and destroys the bacteria which are necessary for the proper sewage treatment. In many rivers, streams, lakes, etc., which act as a water supply for the aforesaid population centers, there are found these unwanted foams and suds. As hereinbefore set forth, the presence of these unwanted foams or suds is due in many instances to the use of detergents which are non-biodegradable in nature and which will not break down by bacterial action thereon. The non-biodegradable nature of these detergents is due to the fact that the alkyl side chain of the molecule is in many instances highly branched and therefore not readily attacked by the organisms which would ordinarily destroy the molecule. In contradistinction to this, the use of straight chain alkyl substituents on the ring will permit the detergents to be destroyed and therefore foams or suds will not build up on the surface of the water.

It is therefore an object of this invention to provide a process for the production of detergents which show biodegradability in both urban and rural sewage disposal systems.

In one aspect an embodiment of this invention resides in a process for the preparation of a biodegradable detergent which comprises the steps of: (a) condensing butadiene with allyl alcohol in a Diels-Alder reaction at a temperature in the range of from about 50° to about 190°C. and a pressure in the range of from atmospheric to about 100 atmospheres to form hydroxymethylcyclohexene; (b) selectively hydrogenating said hydroxymethylcyclohexene to form hydroxymethylcyclohexane; (c) ring alkylating said hydroxymethylcyclohexane with a 1-alkene in the presence of an organic peroxy free-radical generating compound and hydrogen chloride at a temperature at least as high as the decomposition temperature of said free-radical generating compound; (d) alkoxylating the resulting n-alkyl-substituted hydroxymethylcyclohexane with an alkoxylating agent selected from the group consisting of ethylene oxide and propylene oxide at a temperature in the range of from 20° to about 125°C. and a pressure of from about 50 to about 1000 pounds per square inch; and (e) recovering the resultant n-alkyl-substituted hydroxypolyalkoxymethylcyclohexane.

A specific embodiment of this invention is found in a process for the preparation of a biodegradable detergent which comprises the steps of condensing butadiene with allyl alcohol at a temperature in the range of from about 50° to about 190°C. and a pressure in the range of from atmospheric to about 100 atmospheres, selectively hydrogenating the resultant hydroxymethylcyclohexene to form hydroxymethylcyclohexane, ring alkylating said substituted cyclohexane with 1-octene in the presence of di-t-butyl peroxide and hydrogen chloride at a temperature at least as high as the decomposition temperature of said di-t-butyl peroxide, alkoxylating the resultant n-octyl hydroxymethylcyclohexane with ethylene oxide at a temperature in the range of from about 20° to about 125°C. and a pressure in the range of from about 50 to about 1000 pounds per square inch, and recovering the resultant n-octyl hydroxypolyethoxymethylcyclohexane.

Other objects and embodiments will be found in the following further detailed description of the present invention.

As hereinbefore set forth the present invention is concerned with a process for the preparation of detergents which are biodegradable in nature. In addition, the present invention also contemplates the preparation of detergents which are non-ionic or anionic in nature, the process for preparing these compounds being effected in a series of steps. In the first step of the reaction, butadiene is condensed with allyl alcohol in a Diels-Alder type condensation to give 4-hydroxymethylcyclohexene. The Diels-Alder condensation is effected at elevated temperatures, usually in the range of from about 50° to about 190°C. and at a pressure ranging from atmospheric to about 100 atmospheres. The reaction pressure may be afforded by the autogenous pressure of the butadiene or by a combination of butadiene and a substantially inert gas such as nitrogen or argon, the amount of pressure which is utilized being that which is sufficient to maintain at least a portion of the reactants in the liquid phase.

Following the preparation of the 4-hydroxymethylcyclohexane, the compound is then subjected to a selective hydrogenation step prior to alkylation of the compound with a 1-alkene in the presence of a free-radical generating catalyst and hydrogen chloride. The selective hydrogenation of the hydroxymethylcyclohexene is accomplished in the presence of a hydrogenation catalyst comprising a nickel-containing compound or a noble metal-containing compound, these hydrogenation catalysts being well known in the art. Specific examples of these catalysts will include, in particular, platinum and palladium compounds per se or composited on a solid support which is essentially non-acidic in character such as charcoal, kieselguhr, etc.; specific examples being platinum composited on charcoal, platinum composited on kieselguhr, palladium composited on charcoal, nickel composited on kieselguhr, etc. The reaction is effected at hydrogenation conditions which will include a temperature in the range of from about −25° up to about 100°C. and at an applied hydrogen pressure which may range from about 50 to about 2000 pounds per square inch. When these conditions and catalysts are used, the hydroxymethyl substituent remains unchanged, while the cyclohexene ring is hydrogenated to form a cyclohexane ring. Thereafter, the hydroxymethylcyclohexane may be subjected to ring alkylation by reaction with an alpha-olefin in the presence of a free-radical generating compound and hydrogen chloride. It is also contemplated within the scope of this invention that as an alternative variation of this procedure, the hydrogenation of the ring unsaturation may be carried out subsequent to the ring alkylation of the hydroxymethylcyclohexene, i.e., the selective hydrogenation of an n-alkyl hydroxymethylcyclohexene.

The hydroxymethylcyclohexane which has been prepared by the selective hydrogenation hereinbefore set forth is then selectively alkylated utilizing an olefinic hydrocarbon as the alkylating agent. The selective alkylation in which the alkyl substituent is positioned on the ring rather than on the side chain is effected by treating the reactants in the presence of a free-radical generating compound and hydrogen chloride. In the preferred embodiment of the invention, the olefinic hydrocarbon which is utilized as the alkylating agent will comprise a 1-alkene containing from 3 to about 20 carbon atoms in length and preferably from about 6 to about 14 carbon atoms. By utilizing the 1-alkene and an alkylation catalyst comprising a free-radical generating compound and a promoter comprising hydrogen chloride, it is possible to obtain a normal alkyl side chain on the cyclohexane ring rather than a secondary alkyl side chain which would result if the alkylation were effected in the presence of an acidic catalyst of the Friedel-Crafts type or sulfuric acid, etc. Specific examples of the alpha-olefinic hydrocarbons which are utilized as alkylating agents include propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, etc.

The catalysts which are used in this step of the invention will include peroxy compounds, containing the bivalent radical —O—O—, which decomposes to form free radicals which initiate the general reaction and are capable of inducing the condensation of the hydroxymethylcyclohexane with the 1-alkene. Examples of these catalysts include the persulfates, perborates, percarbonates of ammonium and of the alkali metals, or organic peroxy compounds. The organic peroxy compounds constitute a preferred class of catalysts for use in the invention and include peracetic acid, persuccinic acid, methyl ethyl ketone peroxide, methyl isobutyl ketone peroxide, acetyl peroxide, dipropionyl peroxide, di-t-butyl peroxide, butyryl peroxide, lauroyl peroxide, tetralin peroxide, urea peroxide, t-butyl perbenzoate, t-butyl hydroperoxide, methylcyclohexyl hydroperoxide, cumene hydroperoxide, diisopropylbenzene hydroperoxide, etc. Mixtures of peroxy compound catalysts may be employed or the peroxy compound catalyst may be utilized in admixture with various diluents. Thus, organic peroxy compounds which are compounded commercially with various diluents which may be used include benzoyl peroxide compounded with calcium sulfate, benzoyl peroxide compounded with camphor, phthalate esters, etc. Only catalytic amounts (less than stoichiometric amounts) need be used in the process.

The alkylation of the hydroxymethylcyclohexane with the 1-alkene is effected at elevated reaction temperatures which should be at least as high as the initial decomposition temperature of the free-radical generating catalyst, such as the peroxide compound, in order to liberate and form free radicals which promote the reaction. In selecting a particular reaction temperature for use in the process of the present invention, two considerations must be taken into account. First sufficient energy by means of heat must be supplied to the reaction so that the reactants, namely the hydroxymethylcyclohexane and the 1-alkenes will be activated sufficiently for condensation to take place when free radicals are generated by the catalyst. Second, free-radical generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 11 hours at 125° C., 4 hours at 135° C., and 1.5 hours at 145° C. A reaction system temperature must then be selected so that the free-radical generating catalyst decomposes smoothly with the generation of free radicals at a half life which is not too long. In other words, sufficient free radicals must be present to induce the present chain reaction to take place, and these radicals must be formed at a temperature at which the reactants are in a suitably activated state for condensation. When the half life of the free-radical generating catalyst is greater than 10 hours, radicals are not generated at a sufficient rate to cause the reaction of the process of the present invention to go forward at a practically useful rate. Thus, the reaction temperature may be within the range of from about 50° to about 300° C. and at least as high as the decomposition temperature of the catalyst, by which is meant a temperature such that the half life of the free-radical generating catalyst is not greater than 10 hours. Since the half life for each free-radical generating catalyst is different at different temperatures, the exact temperature to be utilized in a particular reaction will vary. However, persons skilled in the art are well acquainted with the half life vs. temperature data for different free-radical generating catalysts. Thus, it is within the skill of one familiar with the art to select the particular temperature needed for any particular catalyst. However, the operating temperatures generally do not exceed the decomposition temperature of the catalyst by more than about 100° C. since free-radical generating catalysts decompose rapidly under such conditions. For example, when a free-radical generating catalyst such as t-butyl perbenzoate is used, having a 10 hour 50% decomposition temperature of approximately 105° C., the operating temperature of the process is from about 105° to about 205° C. When di-t-butyl peroxide having a decomposition temperature of about 125° C. is used, the process is run at a temperature ranging from about 125° to about 225° C. Higher reaction temperatures may be employed, but little advantage is gained if the temperature is more than the hereinbefore mentioned 100° C. higher than the 10 hour, 50 % decomposition temperature of the catalyst. The general effect of increasing the operating temperature is to accelerate the rate of condensation reaction of the hydroxymethylcyclohexane with the 1-alkenes. However, the increased rate of reaction is accompanied by certain amounts of decomposition. In addition to the elevated temperatures which are utilized, the reaction may also be effected at elevated pressures ranging from 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment to charge the reactants and the catalyst to the vessel and to pressure the vessel with 10 or 30 or 50 or more atmospheres of an inert gas such as nitrogen. This helps to insure the presence of liquid phase conditions. However, when the mole quantity of reactants is sufficient, the pressure which they themselves generate at the temperature utilized is sufficient to maintain the desired phase conditions.

Furthermore, the concentration of the catalyst employed in this process may vary over a rather wide range but it is desirable to utilize low concentrations of catalysts such as from about 0.1% to about 10% of the total weight of the combined starting materials charged to the process. The reaction time may be within the range of from less than 1 minute to several hours, depending upon temperature and the half life of the catalyst. Generally speaking, contact times of at least 10 minutes are preferred.

In addition to the free-radical generating catalyst, the alkylation is also effected in the presence of a hydrogen chloride compound. The hydrogen chloride compound is used as a promoter for the reaction and also is used to prevent or inhibit telomerization, said telomerization being a polymerization reaction in which unwanted side reaction products may be formed. The hydrogen chloride may be present as anhydrous hydrogen chloride, as concentrated hydrochloric acid or as an aqueous solution of hydrochloric acid, the hydrochloric acid being present in an amount of from 5 to about 38% in said aqueous solution.

The n-alkyl-substituted hydroxymethylcyclohexane is then subjected to an alkoxylation step to prepare non-ionic biodegradable detergents having the structure:

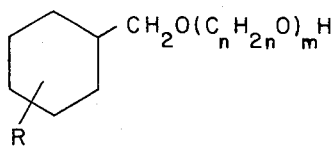

in which R is a normal alkyl radical containing from 3 up to about 20 carbon atoms, $n$ is 2 or 3 and $m$ is an integer ranging from about 1 to about 50 and preferably in a range of from about 3 to about 20. The alkoxylation of the n-alkyl-substituted hydroxymethylcyclohexane is effected by treating the compound with an alkoxylating agent selected from the group consisting of ethylene oxide and propylene oxide in an amount sufficient to produce the desired number of alkoxy units in order that the values hereinbefore set forth for $m$ may be satisfied. In any event, a sufficient amount of alkylene oxide must be used to solubilize the product and maximize its surface active properties either without or with subsequent sulfation.

The alkoxylation is effected by treating the aforementioned compounds with ethylene oxide or propylene oxide at a temperature in the range of from about 20° (ambient) up to about 125° C. and at a pressure in the range of from about 50 to about 1000 pounds per square inch, the presssure being afforded by the alkoxylating agent. In addition, the alkoxylating reaction is effected in the presence of an acidic or basic catalyst. Examples of acidic catalysts which may be employed will include mineral acids such as hydrochloric acid, sulfuric acid, phosphoric acid, etc., organic acids such as methanesulfonic acid, ethanesulfonic acid, benzenesulfonic acid, toluenesulfonic acid, etc. Examples of basic catalysts which may be employed will include sodium carbonate, potassium carbonate, lithium carbonate, sodium acetate, potassium acetate, lithium acetate, sodium propionate, potassium propionate, lithium propionate, sodium hydroxide, potassium hydroxide, lithium hydroxide, the corresponding calcium compounds, magnesium compounds, etc. As hereinbefore set forth a sufficient amount of alkoxylating agent will be used in order that the predetermined value for $m$ in the above formulas is satisfied. Therefore the alkoxylating agent will usually be present in the reaction mixture in a molar excess over that of the n-alkyl-substituted hydroxymethylcyclohexane, said molar excess usually being in a range of from about 5:1 to about 50:1 moles of alkylene oxide per mole of substituted cyclohexane compound.

The process of this invention in which biodegradable detergents of the type hereinbefore set forth in greater detail are prepared may be effected in either a batch or continuous operation. When a batch type operation is used, a quantity of the allyl alcohol is placed in an appropriate apparatus such as an autoclave of the rotating or mixing type. The autoclave is sealed and the butadiene is charged thereto or in an alternate method, a mixture of butadiene and an inert gas such as nitrogen is charged thereto until the desired operating pressure is reached. The autoclave is thereafter heated to the desired operating temperature within the range hereinbefore set forth and maintained thereat for a predetermined residence time which may range from 0.5 up to about 10 hours or more in duration. Upon completion of the desired residence time, heating is discontinued, the autoclave is allowed to return to room temperature, the excess pressure is vented and the reaction mixture is recovered therefrom. The hydroxymethylcyclohexene is separated from any unreacted allyl alcohol by conventional means such as distillation or by any other separation means known in the art and thereafter subjected to a hydrogenation step prior to alkylation with the 1-alkene. In this step the hydroxymethylcyclohexene is selectively hydrogenated by passage over a catalyst of the type hereinbefore set forth in the presence of a hydrogen stream at a temperature ranging from about −25° to about 100° C. and at a hydrogen pressure of from about 50 to about 2000 pounds per square inch, the cyclohexene ring being selectively and relatively completely hydrogenated to form the corresponding cyclohexane ring. The cyclohexane is treated with an alkylating agent by placing said substituted cyclohexane in a second reaction vessel along with a free-radical generating compound and the 1-alkene which is to be utilized as the alkylating agent. This second reaction vessel may be a flask provided with condensing means or an autoclave of the rotating or mixing type. In addition, a promoter comprising hydrogen chloride, either in gaseous form as hydrogen chloride or in aqueous form as hydrochloric acid, is added to the reactor which is thereafter heated to the desired operating temperature which, as hereinbefore set forth, is at least as high as the decomposition temperature of said free-radical generating compound. After maintaining the alkylation reaction at this temperature for a predetermined period of time which may range from about 0.5 up to about 10 hours, heating is discontinued, the reaction mixture is allowed to return to room temperature and the n-alkyl-substituted hydroxymethylcyclohexane is separated and recovered by conventional means.

The n-alkyl-substituted hydroxymethylcyclohexane is then treated with an alkoxylating agent to form the desired product. This treatment is accomplished by placing the substituted cyclohexane in an appropriate apparatus such as a rotating autoclave and the alkoxylating agent is added thereto in a predetermined molor excess so that the finished product will contain the requisite number of alkoxy units in the side chain. In addition, an acidic or basic catalyst of the type hereinbefore set forth in greater detail is also added to the apparatus which is thereafter heated to a predetermined operating temperature. After maintaining the apparatus and contents thereof at this temperature for a period of time which may range from about 0.5 up to about 10 hours or more, the apparatus and contents thereof are allowed to return to room temperature and the product is recovered therefrom and sent to storage.

It is also contemplated within the scope of this invention that the desired product may be prepared while employing a continuous manner of operation. When the continuous manner of operation is to be used, the starting materials comprising the allyl alcohol and butadiene are continuously charged to a reactor which is maintained at the proper operating conditions of temperature and pressure. After passage through this reactor for a predetermined period of time, the effluent is continuously withdrawn, subjected to a separation step whereby the unreacted allyl alcohol and butadiene are separated from the hydroxymethylcyclohexane and recycled to form a portion of the feed stock while the latter is continuously charged to a hydrogenation apparatus along with a stream of hydrogen sufficient to maintain the desired operational pressure. The hydrogen and the hydroxymethylcyclohexene are continuously passed over a hydrogenation catalyst of the type hereinbefore set forth at a temperature in the range of from about −25° to about 100° C. whereby the cyclohexene ring is selectively hydrogenated to form the corresponding cyclohexene ring, and the resulting product is continuously withdrawn. The product which has been selectively hydrogenated to form hydroxymethylcyclohexane is separated from hydrogen, which may be recycled to the hydrogenation step, while the former is thereafter charged to an alkylation reactor which is maintained at the proper operating conditions of temperature and pressure. In addition, the 1-alkene, the free-radical generating compound and the hydrogen chloride promoter are also continuously charged to the apparatus through separate lines or, if so desired, one or more of the reactants may be admixed with another prior to entry into said reactor and the resulting mixture charged thereto in a single stream. After completion of the desired residence time in the alkylation apparatus, the reactor effluent is continuously withdrawn, again subjected to separation steps whereby unreacted starting materials, promoter and by-products are separated from the alkyl-substituted hydroxymethylcyclohexane. The unreacted starting materials are recycled to the apparatus to form a portion of the feed stock while the n-alkyl-substituted hydroxymethylcyclohexane is continuously charged to the alkoxylation reactor. In this reactor the aforementioned substituted cyclohexane is subjected to the action of an alkoxylating agent, said agent, either ethylene oxide or propylene oxide, being continuously charged to the reactor in a molar excess over the charge of cyclohexane. In addition, the catalyst, either acidic or basic in nature, is also charged to the reactor through a separate line or, if so desired, it may be admixed with the carbinol feed and the resulting mixture charged thereto in a single stream. Upon completion of the desired residence time in the alkoxylation reactor, the reactor effluent is withdrawn and subjected to separation means known in the art whereby the desired product, namely, a non-ionic biodegradable detergent comprising an n-alkyl-substituted hydroxypolyalkoxymethylcyclohexane is separated from any unreacted starting materials and recovered, the aforesaid starting materials being recycled to the alkoxylation reactor to form a portion of the feed stock.

The following examples are given to illustrate the process of the present invention which, however, are not intended to limit the generally broad scope of the present invention in strict accordance therewith.

EXAMPLE I

In this example 58 grams (1.0 mole) of allyl alcohol are placed in the glass liner of a rotating autoclave. The liner is sealed into the autoclave and 54 grams (1.0 mole) of butadiene are charged thereto. The autoclave is then heated to a temperature of 125° C. and maintained thereat for a period of 4 hours, at the end of which time heating is discontinued, and the autoclave is allowed to return to room temperature. The autoclave is opened, the reaction mixture is recovered therefrom and subjected to fractional distillation whereby the desired product comprising 4-hydroxymethylcyclohexene is separated from any unreacted allyl alcohol and recovered.

The thus prepared hydroxymethylcyclohexene is then charged to a reactor which is loaded with a catalyst comprising platinum composited on granular charcoal. The 4-hydroxymethylcyclohexene is charged to the reactor at a liquid hourly space velocity of 1 along with a stream of hydrogen in an amount sufficient to maintain a hydrogen pressure of 1000 pounds per square inch, the temperature of the reaction being maintained at 40° C. After passage over the catalyst, the effluent stream is withdrawn to a separation zone wherein the hydrogen gas is separated from the liquid phase, which, upon analysis, is found to be substantially fully hydrogenated to the desired product, hydroxymethylcyclohexane.

The hydroxymethylcyclohexane along with 1-octene, a catalyst comprising di-t-butyl peroxide and concentrated hydrochloric acid is placed in the glass liner of a rotating autoclave and after sealing the autoclave nitrogen is pressed in until an initial pressure of 30 atmospheres is reached. The autoclave and contents thereof are then heated to a temperature of 130° C. and maintained in a range of from 130° to 140° C. for a period of 8 hours. At the end of this time, heating is discontinued, the autoclave is allowed to return to room temperature and the excess pressure is discharged therefrom. The autoclave is opened, the reaction product is recovered and subjected to conventional means of separation whereby the n-octyl-substituted hydroxymethylcyclohexane is separated and recovered.

The aforementioned n-octyl-substituted hydroxymethylcyclohexane is then placed in the glass liner of an autoclave along with a catalyst comprising potassium carbonate. A molar excess of ethylene oxide, in a mole ratio of 10 moles of ethylene oxide per mole of n-octyl-substituted hydroxymethylcyclohexane, is then pressed into the sealed autoclave, and the reactor heated to a temperature of 100° C. for a period of 4 hours. At the end of this time, heating is discontinued, the autoclave is allowed to return to room temperature and the excess pressure is discharged therefrom. The autoclave is opened, and the desired product comprising an n-octyl hydroxypolyethoxymethylcyclohexane is recovered therefrom.

EXAMPLE II

In a manner similar to that set forth in Example I above, 4-hydroxymethylcyclohexene is prepared by condensing allyl alcohol and butadiene in a Diels-Alder reaction. Thereafter, the thus prepared hydroxymethylcyclohexene is selectively hydrogenated by being charged to a reactor which is loaded with a catalyst comprising nickel composited on kieselguhr. The 4-hydroxymethylcyclohexene is charged to this reactor at a liquid hourly space velocity of 1.5 along with a stream of hydrogen, said hydrogen being charged in an amount sufficient to maintain a hydrogen pressure of 1000 pounds per square inch. After passage over the aforesaid catalyst at a temperature of 65° C., the effluent stream is withdrawn to a separation zone in which the hydrogen gas is separated from the liquid phase.

The liquid phase which comprises hydroxymethylcyclohexane is then alkylated by treating a molar excess of cyclohexane with 1-decene in the presence of a catalyst comprising benzoyl peroxide and a promoter comprising concentrated hydrochloric acid at a temperature of from 80° to 90° C. and a nitrogen pressure of 30 atmospheres for a period of 8 hours. The resultant n-decyl hydroxymethylcyclohexane is thereafter alkoxylated by reacting said substituted cyclohexane with propylene oxide in the presence of potassium carbonate, the mole ratio of propylene oxide to substituted cyclohexane being 8 moles of propylene oxide per mole of substituted cyclohexane. The alkoxylation is effected in a sealed autoclave at a temperature of 100° C. for a period of 4 hours. At the end of the 4-hour heating period, the autoclave is allowed to return to room temperature, any excess pressure is vented and the desired product comprising an n-decyl hydroxypolypropoxymethylcyclohexane is recovered therefrom.

EXAMPLE III

To a reactor which is loaded with a hydrogenation catalyst comprising nickel composited on kieselguhr is charged 4-hydroxymethylcyclohexene which is prepared from the Diels-Alder condensation of allyl alcohol and butadiene in a manner similar to that set forth in Example I above. The 4-hydroxymethylcyclohexene, as in the above examples, is charged to the reactor at a liquid hourly space velocity of 1 along with a stream of hydrogen which is sufficient to maintain a hydrogen pressure of 1000 pounds per square inch, the reactor being maintained at a temperature of about 60° C. After passage over the catalyst, the effluent stream is withdrawn to a separation zone wherein the hydrogen gas is separated from the liquid phase, the latter comprising the selectively hydrogenated product, namely, hydroxymethylcyclohexane.

A molar excess of the aforementioned hydroxymethylcyclohexane along with an alkylating agent comprising 1-dodecene, benzoyl peroxide, and concentrated hydrochloric acid comprising the reaction mixture is placed in an alkylation apparatus and heated to a temperature in the range of from 90° to 95° C. for a period of 4 hours. At the end of the 4-hour period, heating is discontinued, the reactor is allowed to return to room temperature and the mixture is subjected to fractional distillation whereby the desired product comprising n-dodecyl-substituted hydroxymethylcyclohexane is recovered.

The substituted cyclohexane is then placed in the glass liner of a rotating autoclave along with a catalytic amount of hydrochloric acid. Following this, ethylene oxide is pressed into the reactor in a mole ratio of 10 moles of ethylene oxide per mole of substituted cyclohexane. The reactor is sealed and heated to a temperature of 75° C. for a period of 4 hours, at the end of which time heating is discontinued, the autoclave is allowed to return to room temperature, the excess pressure is discharged and the reaction mixture is recovered. The mixture is then subjected to fractional distillation under reduced pressure whereby the desired product comprising an n-dodecyl hydroxypolyethoxymethylcyclohexane is separated and recovered.

EXAMPLE IV

In this example, 4-hydroxymethylcyclohexene which is prepared by the Diels-Alder reaction between allyl alcohol and butadiene in a manner hereinbefore described is charged to a reactor containing a hydrogenation catalyst comprising platinum composited on kieselguhr. As in the above examples, the substituted cyclohexene is charged at a liquid hourly space velocity of 1 accompanied by a stream of hydrogen which is sufficient to maintain a hydrogen pressure of 1000 pounds per square inch, said hydrogenation reaction being effected at a temperature of 40° C. After passage over the aforesaid hydrogenation catalyst, the effluent stream is recovered and gaseous hydrogen is separated therefrom. The liquid product which comprises the selectively hydrogenated compound, hydroxymethylcyclohexane, is then charged to a second reactor which contains a catalyst comprising di-t-butyl peroxide and a promoter comprising concentrated hydrochloric acid. In addition, the alkylating agent comprising 1-tridecene is also placed in the reactor which is thereafter sealed and heated to a temperature of 130° C. The reactor and contents thereof are maintained at a temperature in the range of from 130° to 140° C. for a period of 4 hours, at the end of which time heating is discontinued and the autoclave is allowed to return to room temperature. The autoclave is opened and the desired product comprising n-tridecyl hydroxymethylcyclohexane is separated and recovered from any unreacted starting materials which still may be present. Following this, the substituted cyclohexane is placed in a third reactor containing a sodium carbonate catalyst and a sufficient amount of ethylene oxide is charged thereto so that said ethylene oxide is present in a molar excess of 12 moles per mole of substituted cyclohexane. The reactor is then heated to a temperature of 75° C. and maintained thereat for a period of 4 hours, at the end of which time heating is discontinued. After allowing the autoclave to return to room temperature any excess pressure is discharged and the autoclave is opened. The reaction mixture is recovered and subjected to fractional distillation under reduced pressure whereby the desired n-tridecyl hydroxypolyethoxymethylcyclohexane is separated and recovered.

EXAMPLE V

In like manner, 4-hydroxymethylcyclohexene which is prepared by the Diels-Alder condensation between allyl alcohol and butadiene in the manner hereinbefore set forth is selectively hydrogenated by passing said compound over a hydrogenation catalyst comprising platinum composited on granular charcoal along with a stream of hydrogen, the reaction conditions including a temperature of 40° C., a hydrogen pressure of 1000 pounds per square inch and a liquid hourly space velocity of 1. The selectively hydrogenated hydroxymethylcyclohexane is separated from the hydrogen gas and alkylated by treatment with an alkylating agent comprising 1-tetradecene. The alkylating step is effected in the presence of a catalyst comprising di-t-butyl peroxide and a promoter comprising hydrogen chloride, the reaction conditions for said alkylation step including a temperature in the range of from 130° to 140° C. at a nitrogen pressure of 30 atmospheres for a period of 8 hours. In a manner similar to that hereinbefore set forth, the desired n-tetradecyl hydroxymethylcyclohexane is recovered and subjected to an alkoxylation step. This step is effected by treating the substituted cyclohexane with a molar excess of 9 moles of propylene oxide per mole of substituted cyclohexane in a reactor containing the sodium carbonate catalyst. The alkoxylation conditions for this step of the process will include a temperature in the range of from about 75° to about 80° C. and a reaction time of 4 hours. The desired product comprising an n-tetradecyl hydroxypolypropoxymethylcyclohexane is separated and recovered by conventional means.

I claim as my invention:

1. A process for the preparation of a biodegradable detergent which comprises the steps of:
   a. condensing butadiene with allyl alcohol in a Diels-Alder reaction at a temperature in the range of from about 50° to about 190° C. and a pressure in the range of from atmospheric to about 100 atmospheres to form hydroxymethylcyclohexene;
   b. selectively hydrogenating said hydroxymethylcyclohexene to form hydroxymethylcyclohexane;
   c. ring alkylating said hydroxymethylcyclohexane with a 1-alkene in the presence of an organic peroxy free-radical generating compound and hydrogen chloride at a temperature at least as high as the decomposition temperature of said free-radical generating compound;
   d. alkoxylating the resultant n-alkyl-substituted hydroxymethylcyclohexane with an alkoxylating agent selected from the group consisting of ethylene oxide and propylene oxide at a temperature in the range of from 20° to about 125° C. and a pressure of from about 50 to about 1000 pounds per square inch; and
   e. recovering the resultant n-alkyl-substituted hydroxypolyalkoxymethylcyclohexane.

2. The process as set forth in claim 1 in which said 1-alkene contains from 3 to about 20 carbon atoms.

3. The process as set forth in claim 1 in which said 1-alkene is 1-octene, said alkoxylating agent is ethylene oxide, and said n-alkyl-substituted hydroxymethylcyclohexane is n-octyl hydroxypolyethoxymethylcyclohexane.

4. The process as set forth in claim 1 in which said 1-alkene is 1-decene, said alkoxylating agent is propylene oxide, and said n-alkyl-substituted hydroxymethylcyclohexane is n-decyl hydroxypolypropoxymethylcyclohexane.

5. The process as set forth in claim 1 in which said 1-alkene is 1-dodecene, said alkoxylating agent is ethylene oxide, and said n-alkyl-substituted hydroxymethylcyclohexane is n-dodecyl hydroxypolyethoxymethylcyclohexane.

6. The process as set forth in claim 1 in which said 1-alkene is 1-tridecene, said alkoxylating agent is ethylene oxide, and said n-alkyl-substituted hydroxymethylcyclohexane is n-tridecyl hydroxypolyethoxymethylcyclohexane.

7. The process as set forth in claim 1 in which said 1-alkene is 1-tetradecene, said alkoxylating agent is propylene oxide, and said n-alkyl-substituted hydroxymethylcyclohexane is n-tetradecyl hydroxypolypropoxymethylcyclohexane.

* * * * *